US012583894B2

(12) United States Patent
Vedam-Mai et al.

(10) Patent No.: US 12,583,894 B2
(45) Date of Patent: Mar. 24, 2026

(54) MATERIALS AND METHODS FOR THE TREATMENT OF LEWY BODY DISORDERS

(71) Applicant: UNIVERSITY OF FLORIDA RESEARCH FOUNDATION, INC., Gainesville, FL (US)

(72) Inventors: Vinata Vedam-Mai, Gainesville, FL (US); Michael S. Okun, Gainesville, FL (US); Catherine Flores, Gainesville, FL (US); Duane Mitchell, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 922 days.

(21) Appl. No.: 17/044,045

(22) PCT Filed: Apr. 3, 2019

(86) PCT No.: PCT/US2019/025596
§ 371 (c)(1),
(2) Date: Sep. 30, 2020

(87) PCT Pub. No.: WO2019/195432
PCT Pub. Date: Oct. 10, 2019

(65) Prior Publication Data
US 2021/0093670 A1 Apr. 1, 2021

Related U.S. Application Data

(60) Provisional application No. 62/652,759, filed on Apr. 4, 2018.

(51) Int. Cl.
| | |
|---|---|
| *A61K 39/00* | (2006.01) |
| *A61K 40/11* | (2025.01) |
| *A61K 40/19* | (2025.01) |
| *A61K 40/24* | (2025.01) |
| *A61K 40/41* | (2025.01) |
| *A61P 25/28* | (2006.01) |
| *C07K 14/47* | (2006.01) |
| *C12N 5/0783* | (2010.01) |

(52) U.S. Cl.
CPC .......... *C07K 14/47* (2013.01); *A61K 39/0007* (2013.01); *A61K 40/11* (2025.01); *A61K 40/19* (2025.01); *A61K 40/24* (2025.01); *A61K 40/414* (2025.01); *A61P 25/28* (2018.01); *C12N 5/0636* (2013.01); *C12N 2502/1121* (2013.01)

(58) Field of Classification Search
CPC .... A61K 39/0007; A61K 40/19; A61K 40/24; A61K 40/414; A61P 25/28; C12N 2502/1121
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,734,014 B1* | 5/2004 | Hwu .................... | C12N 5/0639 435/325 |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 8,809,505 B2 | 8/2014 | Zweckstetter et al. | |
| 2006/0121005 A1 | 6/2006 | Berenson et al. | |
| 2009/0053249 A1* | 2/2009 | Qi .......................... | C12N 15/86 435/375 |
| 2014/0363447 A1 | 12/2014 | Kasrayan et al. | |
| 2017/0196948 A1 | 7/2017 | Cao et al. | |

FOREIGN PATENT DOCUMENTS

| | | |
|---|---|---|
| WO | WO-2009133521 A2 | 11/2009 |
| WO | 2012/129514 A1 | 9/2012 |

OTHER PUBLICATIONS

Kao et al. A New Strategy for Tumor Antigen Discovery Based on in Vitro Priming of Naive T Cells with Dendritic Cells. Clinical Cancer Research. vol. 7, 773s-780s, (Year: 2001).*
Ugen et al. Evaluation of an a synuclein sensitized dendritic cell based vaccine in a transgenic mouse model of Parkinson disease. Human Vaccines & Immunotherapeutics vol. 11, 2015—Issue 4 (Year: 2015).*
Bartels et al., N-alpha-acetylation of a-synuclein increases its helical folding propensity, GM1 binding specificity and resistance to aggregation, PLoS One, 9(7):e103727 (2014).
Beyer, Alpha-synuclein structure, posttranslational modification and alternative splicing as aggregation enhancers, Acta Neuropathol., 112(3):237-251 (2006).
Braak et al., Staging of brain pathology related to sporadic Parkinson's disease, Neurobiology of Aging, 24(2):197-211 (2003).
Chartier-Harlin et al., Alpha-synuclein locus duplication as a cause of familial Parkinson's disease, Lancet., 364:1167-1169 (2004).

(Continued)

*Primary Examiner* — Taeyoon Kim
(74) *Attorney, Agent, or Firm* — MARSHALL, GERSTEIN & BORUN LLP

(57) ABSTRACT

The present disclosure provides methods for reducing Lewy Bodies in the central nervous system of a subject in need thereof by administering a T cell that is specific for an α-synuclein mutant to the subject.

7 Claims, 5 Drawing Sheets
Specification includes a Sequence Listing.

(56)                    References Cited

OTHER PUBLICATIONS

Clayton et al., The synucleins: a family of proteins involved in synaptic function, plasticity, neurodegeneration and disease, Trends Neurosci., 21(6):249-254 (1998).

Conway et al., Accelerated in vitro fibril formation by a mutant alpha-synuclein linked to early-onset Parkinson disease, Nat. Med., 4(11):1318-1320 (1998).

Dieckmann et al., Optimizing the exogenous antigen loading of monocyte-derived dendritic cells, Int. Immunol., 17(5):621-635 (2005).

Fuchs et al., Phenotypic variation in a large Swedish pedigree due to SNCA duplication and triplication, Neurology, 68(12):916-922 (2007).

Ibanez et al., Causal relation between alpha-synuclein gene duplication and familial Parkinson's disease, Lancet., 364:1169-1171 (2004).

International Application No. PCT/US19/25596, International Preliminary Report on Patentability, mailed Oct. 15, 2020.

International Application No. PCT/US19/25596, International Search Report and Written Opinion, mailed Jun. 24, 2019.

Janeway, The priming of helper T cells, Semin. Immunol., 1(1):13-20 (1989).

Kellie et al., Quantitative measurement of intact alpha-synuclein proteoforms from post-mortem control and Parkinson's disease brain tissue by intact protein mass spectrometry, Sci. Rep., 4:5797 (2014).

Lesage et al., G51D a-synuclein mutation causes a novel parkinsonian-pyramidal syndrome, Ann. Neurol., 73(4):459-471 (2013).

Maraganore et al., Collaborative analysis of alpha-synuclein gene promoter variability and Parkinson disease, JAMA, 296(6):661-670 (2006).

Nishioka et al., Expanding the clinical phenotype of SNCA duplication carriers, Mov. Disord., 24(12):1811-1819 (2009).

Pals et al., alpha-Synuclein promoter confers susceptibility to Parkinson's disease, Ann. Neurol., 56(4):591-595 (2004).

Pankratz et al., Genomewide association study for susceptibility genes contributing to familial Parkinson disease, Hum. Genet., 124(6):593-605 (2009).

Polymeropoulos et al., Mutation in the alpha-synuclein gene identified in families with Parkinson's disease, Science, 276:2045-2047 (1997).

Proukakis et al., A novel a-synuclein missense mutation in Parkinson disease, Neurology, 80(11):1062-1064 (2013).

Rajput et al., Alpha-synuclein polymorphisms are associated with Parkinson's disease in a Saskatchewan population, Mov. Disord., 24(16):2411-2414 (2009).

Singleton et al., alpha-Synuclein locus triplication causes Parkinson's disease, Science, 302:841 (2004).

Spillantini et al., Alpha-synuclein in Lewy bodies, Nature, 388:839-840 (1997).

Ueda et al., Molecular cloning of cDNA encoding an unrecognized component of amyloid in Alzheimer disease, Proc. Natl. Acad. Sci. USA, 90(23):11282-6 (1993).

Zarranz et al., The new mutation, E46K, of alpha-synuclein causes Parkinson and Lewy body dementia, Ann. Neurol., 55(2):164-173 (2004).

Ugen et al., "Evaluation of an [alpha] synuclein sensitized dendritic cell based vaccine in a transgenic mouse model of Parkinson disease", Human Vaccines & Immunotherapeutics, vol. 11, No. 4, pp. 922-930, XP055886524, Feb. 25, 2015.

* cited by examiner

MATERIALS AND METHODS FOR THE TREATMENT OF LEWY BODY DISORDERS

CROSS-REFERENCE TO RELATED APPLICATIONS

The present application claims the benefit of priority to U.S. Provisional Application No. 62/652,759, filed Apr. 4, 2018, the disclosure of which is incorporated herein by reference in its entirety.

FIELD OF THE INVENTION

The present disclosure provides methods for reducing Lewy Bodies in the central nervous system of a subject in need thereof by administering a T cell that is specific for an α-synuclein mutant.

INCORPORATION BY REFERENCE OF MATERIALS SUBMITTED ELECTRONICALLY

This application contains, as a separate part of the disclosure, a Sequence Listing in computer readable form (Filename: 52761_Seqlisting.txt; Size: 1,554 bytes; Created: Apr. 3, 2019), which is incorporated by reference in its entirety.

BACKGROUND

Parkinson's disease is characterized by a progressive loss of dopamine (DA) neurons of the nigrostriatal system and by the presence of Lewy bodies (LB) and neurites (LN), proteinaceous intraneuronal inclusions mainly composed of filamentous alpha-synuclein aggregates. The staging of brain pathology related to sporadic PD is reported by Braak et al (Neurobiology of aging 24 (2003) 197-211).

Synucleinopathies are a diverse group of neurodegenerative disorders that share a common pathologic lesion containing abnormal aggregates of insoluble α-synuclein protein in selectively vulnerable populations of neurons and glia. Certain evidence links the formation of abnormal filamentous aggregates to the onset and progression of clinical symptoms and the degeneration of affected brain regions in neurodegenerative disorders including Parkinson's disease (PD), diffuse Lewy body disease (DLBD), multiple system atrophy (MSA), and disorders of brain iron concentration. The current treatment option for these diseases include symptomatic medications such as carbidopa-levodopa, anticholinergics, and monoamine oxidase inhibitors, with widely variable benefit. Even for the best responders, i.e., patients with idiopathic Parkinson's Disease, an initial good response to levodopa is typically overshadowed by drug-induced complications such as motor fluctuations and debilitating dyskinesia. Given the severe debilitating nature of these disorders and their prevalence, there is a clear need in the art for novel approaches for treating and managing these diseases.

SUMMARY

The present disclosure is based on the discovery that adoptive immunotherapy targeting α-synuclein mutant protein in the central nervous effectively reduces the presence of the Lewy Bodies in a subject.

In one aspect, described herein is a method of reducing Lewy Bodies in the central nervous system of a subject, the method comprising administering to a subject in need thereof a T cell that is specific for an α-synuclein (α-syn) mutant in an amount effective to reduce Lewy Bodies in the subject. In some embodiments, the T cell is derived from the subject (i.e., autologous).

In some embodiments, the method comprises contacting the T cell with an α-syn mutant antigen ex vivo prior to the administering step. In some embodiments, prior to the administration step, the method comprises detecting an α-syn mutation (e.g., a human α-syn mutant) in the subject and, optionally, exposing the T cells to an antigen comprising the α-syn mutation. In some embodiments, the α-syn mutant comprises a mutation selected from the group consisting of A53T, A30P, E46K, H50Q, and G51D and combinations thereof with reference to SEQ ID NO: 1 (human α-syn).

In some embodiments, the subject has a disorder selected from the group consisting of Parkinson's disease (including idiopathic Parkinson's disease (PD)), Diffuse Lewy Body Disease (DLBD) (also known as Dementia with Lewy Bodies (DLB)), Combined Alzheimer's and Parkinson disease, multiple system atrophy (MSA), Lewy body dysphagia, Incidental LBD, Inherited LBD (e.g., typically involving mutations of the alpha-synuclein gene, PARK3 and PARK4), and Multiple System Atrophy (e.g., Olivopontocerebellar Atrophy, Striatonigral Degeneration, and Shy-Drager Syndrome). DLBD shares symptoms of both Alzheimer's and Parkinson's disease. DLBD differs from Parkinson's disease mainly in the location of Lewy Bodies. In DLBD, Lewy Bodies form mainly in the cortex; in Parkinson's disease, they form mainly in the substantia nigra.

In some embodiments, the Lewy Bodies are reduced in the brain and/or spinal cord of the subject following administration. In some embodiments, the Lewy Bodies are reduced by at least 10% (or at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more) in the brain and/or spinal cord of the subject.

The disclosure also provides a composition comprising a dendritic cell modified to express an α-synuclein (α-syn) mutant, a T cell and a pharmaceutically acceptable carrier.

DETAILED DESCRIPTION

Figure 1:
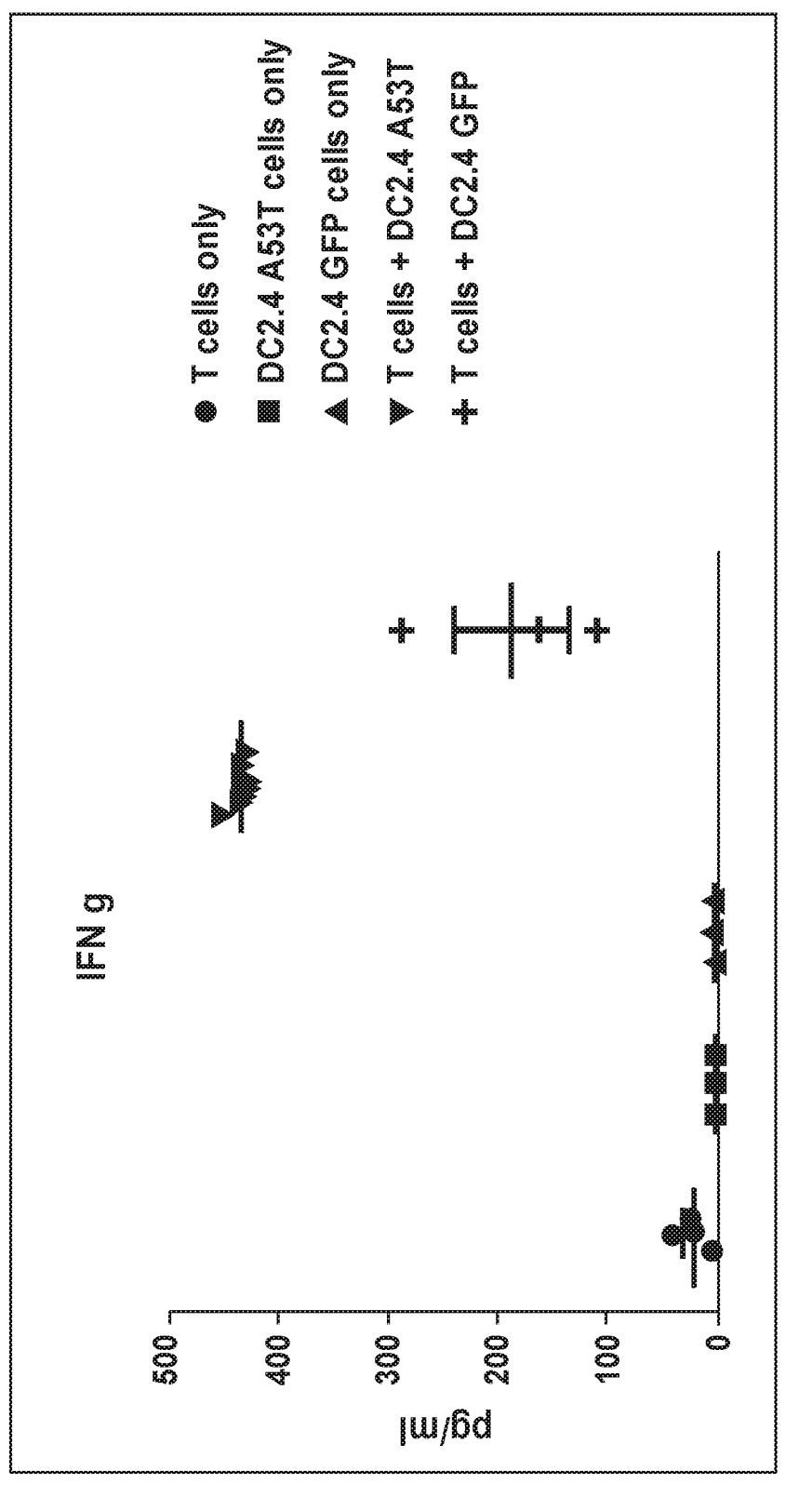
FIG. 1 shows that A53T α-synuclein specific T cells secrete IFN-γ.

Adoptive immunotherapy involves the activation and expansion of immune cells ex vivo, with the resulting cells transferred to the patient to treat disease. Described herein is a method of reducing Lewy Bodies in the central nervous system of a subject, the method comprising administering to a subject in need thereof a T cell that is specific for an α-synuclein (α-syn) mutant in an amount effective to reduce Lewy Bodies in the subject. The phrase "T cell that is specific for an α-synuclein mutant" as used herein means a T cell that is able to recognize an α-synuclein mutant (e.g., α-synuclein mutant in the context of a major histocompatibility complex (MHC)) in a sample, but that does not substantially recognize or bind irrelevant antigen/MHC in a sample.

Alpha-synuclein

The method of the disclosure comprises administering to a subject in need thereof a T cell that is specific for an α-syn mutant. In some embodiments, the α-syn mutant is a human α-syn mutant. Alpha-synuclein is a protein which, in the brain, plays a central role in the control of dopaminergic neuronal functions and which is thought to be critically implicated in PD pathophysiology. Human alpha-synuclein is a peptide of 140 amino acids having the following amino acid sequence: (SEQ ID NO:1) MDVFMKGLSK AKEG-VVAAAE KTKQGVAEAA GKTKEGVLYV GSKTKEG-VVH GVATVAEKTK EQVTNVGGAV VTGVTAVAQK TVEGAGSIAA ATGFVKKDQL GKNEEGAPQE GILEDMPVDP DNEAYEMPSE EGYQDYEPEA (Ueda et al., Proc. Natl. Acad. Sci. USA (1993) 90:11282-6); Gen-Bank accession number: P37840).

Apart from the predominant 140 amino acid protein, there are at least two other alternatively spliced variants of the protein; the 126 amino acid and 112 amino acid variants that lack exon 3 and exon 5, respectively (Beyer et al., Acta Neuropathol., 112: 237-251, 2006). The α-synuclein protein has three distinct structural domains: (1) a amphipathic N-terminal region (residues 1 to 60 of SEQ ID NO: 1) containing 11 amino acid repeats including the consensus sequence KTKEGV, which is important in α-helix formation (Clayton et al., Trends Neurosci., 21: 249-254, 1998); (2) a central hydrophobic region (residues 61 to 95 of SEQ ID NO: 1) containing the non-amyloid component region, which is important in protein aggregation (Spillantini et al., Nature, 388: 839-840, 1997); and (3) a C-terminal region (residues 96 to 140 of SEQ ID NO: 1) is highly acidic and proline rich. The vast majority of α-syn in human brain is N-terminally acetylated (Kellie, J. F., et al., Sci. Rep. 4 (2014) 5797), and this N-terminal acetylation inhibits α-syn from aggregation (Bartels, T., et at, PLoS One 9 (2014) e103727). Alpha-synuclein fibrillar aggregates are a component of Lewy bodies and Lewy neurites.

Alpha-synuclein is encoded by the SNCA gene. PD genome-wide association studies have shown that single nucleotide polymorphisms in SNCA are strongly associated with an increased risk for idiopathic PD (Pals et al., Ann. Neurol., 56:591-595, 2004; Rajput et al., Mov. Disord., 24:2411-2414, 2009; Pankratz et al., Hum. Genet., 124:593-

605, 2009; Maraganore et al., JAMA, 296:661-670, 2006). The SNCA missense mutation A53T was the first causal mutation identified in dominantly inherited PD (Polymeropoulos et al., Science, 276:2045-2047, 1997; Zarranz et al., Ann. Neurol., 55:164-173, 2004; Proukakis et al., 80:1062, 1064, 2013; Lesage et al., Ann. Neurol., 73:459-471, 2013). SNCA missense mutations accelerates α-synuclein fibril formation in vitro, implicating α-synuclein misfolding and aggregation in PD pathogenesis (Conway et al., Nat. Med., 4:1318-1320, 1998). SNCA duplication and triplication have also been identified in PD subjects (Singleton et al., Science, 302:841, 2004; Chartier-Harlin et al., Lancet, 364:1167-1169, 2004; Ibanez et al., Lancet, 364:1169-1171, 2004; Fuchs et al., Neurology, 68:916-922, 2007 and Nishioka et al., Mov. Disord., 24:1811-1819, 2009). Additional examples of α-synuclein mutants can be found in U.S. Pat. No. 8,809,505, the disclosure of which is incorporated herein by reference in its entirety.

The term α-synuclein "mutant" means that at least one amino acid residue of the wild type α-synuclein molecule is deleted, inserted, or replaced by another amino acid residue. The techniques of molecular biology to generate these deletions, insertions or substitutions are well-known in the art. Typically, the mutant α-synuclein does not have 100% amino acid sequence identity to SEQ ID NO: 1. In those cases, a mutant α-synuclein is present if there is a difference of at least one residue on the amino acid sequence level between the sequence of interest and SEQ ID NO: 1.

A polypeptide has "at least X % identity" to SEQ ID NO: 1 if SEQ ID NO: 1 is aligned with the best matching sequence of a polypeptide of interest, and the amino acid identity between those two aligned sequences is at least X %. Such an alignment of amino acid sequences can be performed using, for example, publicly available computer homology programs such as the "BLAST" program provided on the NCBI homepage at http://www.ncbi.nlm.nih-.gov/blast/blast.cgi, using the default settings provided therein. Further methods of calculating sequence identity percentages of sets of amino acid sequences or nucleic acid sequences are known in the art. The term "at position X" as used herein refers to the amino acid numbering according to SEQ ID NO: 1. An alignment of an amino acid sequence of interest with SEQ ID NO: 1 allows determining a corresponding amino acid (residue) in the amino acid sequence of interest. In some embodiments, the mutant alpha-synuclein has at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5% amino acid sequence identity to SEQ ID NO: 1.

In some embodiments, the mutant α-synuclein is a human α-synuclein protein. In some embodiments, the mutant α-synuclein is an α-synuclein from a non-human species. Exemplary non-human species of α-synuclein include, but are not limited to, the α-synuclein of *Pan troglodytes* (accession number XP-001162416.1), *Pan paniscus* (accession number AAQ85068.1), *Gorilla gorilla* (accession number AAQ85072.1), *Erythrocebus patas* (accession number AAQ85067.1), *Macaca fascicularis* (accession number AAQ85071.1), *Macaca mulatta* (accession number AAQ85074), *Pongo abelii* (accession number AAQ85070.1), *Saguinus labiatus* (accession number AAQ85075.1), *Sus scrofa* (accession number NP-001032222.1), *Lagothrix lagotricha* (accession number AAQ85073.1), *Ateles geoffroyi* (accession number AAQ85076.1), *Canis familiaris* (accession number XP-535656.1), *Rattus norvegicus* (accession number NP-062042.1), *Mus musculus* (accession number NP-001035916), *Bos Taurus* (accession number NP-001029213.1), *Equus caballus* (accession number XP-001496954.1), *Gallus gallus* (accession number NP 990004.1), *Taeniopygia guttata* (accession number NP-001041718.1), *Xenopus laevis* (accession number NP-001080623.1), and *Xenopus tropicalis* (accession number NP-001090876.1). In instances where the subject is a human and a non-human α-synuclein is used to activate a T cell, the homolog selected should elicit a T cell response against the human α-synuclein mutant.

In some embodiments, the α-synuclein mutant comprises an amino acid substitution of at least one position selected from the group consisting of amino acid positions 30, 46, 50, 51, and 53, or a combination of any of the foregoing, within the α-synuclein sequence (e.g., SEQ ID NO: 1). In some embodiments, the α-synuclein mutant comprises an amino acid substitution selected from the group consisting of A53T, A30P, E46K, H50Q and G51D, or a combination of any of the foregoing.

Source and Priming of T Cells

The method described herein comprises the step of administering a T cell that is specific for an α-synuclein mutant to a subject in need thereof.

The T cells may originate from a donor (i.e., heterologous) or may be derived from the ultimate recipient of the treatment (i.e., autologous). Alternatively, the T cells may be derived from an established T lymphocyte cell line (i.e., a commercially available T cell line). A population of T cells can be obtained from a subject just prior to priming for administration to a subject in need thereof, or can be collected earlier in time and, optionally, frozen for later use. In some embodiments, the T cell population is taken from a generally healthy subject. In some embodiments, the T cell population is taken from a generally healthy subject who is at risk of developing a disease, but who has not yet developed a disease, and the cells of interest are isolated and frozen for later use. In various aspects, the cells are collected from a subject prior to receiving relevant treatment modalities, including, but not limited to, treatment with agents such as carbidopa-levodopa (Sinemet®), cholinesterase inhibitors, dopamine agonists (e.g., Mirapex, Apokyn, Ropinirole), monoamine oxidase B (MAO-B) inhibitors (e.g., Seligiline, Rasagiline) and catechol-O-methyl transferase (COMT) inhibitors (e.g., COMtan, Stalevo)

T cells can be obtained from a number of sources, including peripheral blood mononuclear cells, bone marrow, lymph node tissue, cord blood, thymus tissue, tissue from a site of infection, ascites, pleural effusion, spleen tissue, and tumors. A number of techniques are available for collecting T cells from a subject and isolating T cells from other cell types (e.g., FICOLL™ separation). In some embodiments, cells from the circulating blood of a subject are obtained by apheresis. The apheresis product typically contains T cells, monocytes, granulocytes, B cells, other nucleated white blood cells, red blood cells, and platelets. In some embodiments, the cells collected by apheresis are washed to remove the plasma fraction and to place the cells in an appropriate buffer or media for subsequent processing steps. The cells can be washed with phosphate buffered saline (PBS) or a wash solution lacking calcium, magnesium, or other divalent cations. A washing step may be accomplished by methods known to those in the art, such as by using a semi-automated "flow-through" centrifuge (for example, the Cobe 2991 cell processor, the Baxter CytoMate, or the Haemonetics Cell Saver 5). After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

Optionally, T cells are isolated from other cells by, e.g., lysing red blood cells and depleting monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive and/or negative selection techniques. Positive and negative selection techniques are well known in the art. For example, enrichment of a desired cell population employing negative selection techniques involves, e.g., cell sorting and/or selection via negative magnetic immunoadherence or flow cytometry that uses a cocktail of monoclonal antibodies directed to cell surface markers present on the negatively selected cells. The skilled artisan would recognize that multiple rounds of selection can be used. In certain embodiments, it may be desirable to perform the selection procedure and use "unselected" cells in the activation and expansion process. "Unselected" cells can also be subjected to further rounds of isolation from other cell types. If desired, a population of cells can be frozen during processing to achieve a T cell population for administration. While not wishing to be bound by any particular theory, a freeze and subsequent thaw step may provide a more uniform product by removing granulocytes and, to some extent, monocytes in the cell population. After the washing step, the cells may be suspended in a freezing solution. While many freezing solutions and parameters are known in the art and will be useful in this context, various methods employ PBS containing 20% DMSO and 8% human serum albumin; or culture media containing 10% Dextran 40 and 5% Dextrose, 20% Human Serum Albumin and 7.5% DMSO; or 31.25% Plasmalyte-A, 31.25% Dextrose 5%, 0.45% NaCl, 10% Dextran 40 and 5% Dextrose, 20% Human Serum Albumin, and 7.5% DMSO. Other suitable cell freezing media contains, for example, Hespan and PlasmaLyte A. In an exemplary method, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed and allowed to rest for a period of time (e.g., one hour or longer) at room temperature prior to activation.

The disclosure also contemplates a method further comprising preparing a T cell population for use in adoptive immunotherapy. In this regard, the method comprises activating T cells with antigen-loaded dendritic cells (DCs); expanding the activated T cells in culture; and reintroducing the activated T cells back into the subject. The T cells can be activated and expanded using any suitable method, including methods known in the art such as, for example, the illustrative methods disclosed in Janeway, Semin Immunol., 1(1):13-20, 1989 and U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and patent publication nos. WO2012/129514 and US20060121005, the disclosure of which are incorporated herein by reference in their entireties. In one embodiment, the dendritic cells are cultured in medium containing the antigen (e.g., α-syn mutant). The DCs then take up and process the antigen on the cell surface in association with MHC molecules. In some embodiments, the DCs are loaded with the antigen of interest by transfection with a nucleic acid encoding the antigen as described, for example, in Example 1. Methods of producing antigen-loaded DCs are known to those of skill in the art. See, e.g., Dieckmann et al., International Immunology, Volume 17, Issue 5, 1 May 2005, Pages 621-635.

In some embodiments, the methods described herein comprise the step of determining the presence of an α-syn mutant in a sample from the subject, and subsequently activating the T cell to be specific for the α-syn mutant. For example, the method optionally comprises determining the presence of an A53T α-syn mutant in a sample from the subject and activating the T cell against the A53T mutant. In this regard, mutant α-syn from the subject is used to generate antigen-loaded dendritic cells, which are then employed to activate T cells to generate a population of T cells targeting the particular α-syn mutant derived from the subject.

Conditions appropriate for T cell culture (which may or may not include other cell types, such as dendritic cells) include an appropriate media (e.g., Minimal Essential Media or RPMI Media 1640 AIM-V, DMEM, MEM, α-MEM, F-12, X-vivo 15 X-Vivo 20, or Optimizer) that may contain factors to promote proliferation and viability, including serum (e.g., fetal bovine or human serum), cytokines (e.g., interleukin-2 (IL-2), insulin, IFN-gamma, IL-4, IL-7, GM-CSF, IL-10, IL-12, IL-15, TGFβ, and/or TNF-α), amino acids, sodium pyruvate, or vitamins. Other additives for the growth of cells include, but are not limited to, surfactant, plasmanate, and reducing agents such as N-acetyl-cysteine and 2-mercaptoethanol. Antibiotics, e.g., penicillin and streptomycin, are generally included in experimental cultures, but not in cultures that are to be infused into a subject. The cells are maintained under conditions necessary to support growth, for example, an appropriate temperature (e.g., 37° C.) and atmosphere (e.g., air plus 5% $CO_2$).

Compositions for Administration

The disclosure provides compositions comprising T cells that target an α-synuclein (α-syn) mutant (e.g., an α-syn mutant comprising an amino acid substitution selected from the group consisting of A53T, A30P, E46K, H50Q and G51D, or combinations thereof). Such compositions can be administered to subjects in the method described further herein.

In some embodiments, the cells are formulated by first harvesting them from their culture medium, and then washing and concentrating the cells in a formulation and container system suitable for administration (a "pharmaceutically acceptable" carrier) in a treatment-effective amount. Suitable formulations are known in the art and include, e.g., normal saline, Normosol-R (Abbott) or Plasma-Lyte A (Baxter), 5% dextrose in water, or Ringer's lactate. The infusion medium can be supplemented with human serum albumin. Formulations suitable for administration also may include, e.g., antioxidants, buffers, bacteriostats, solutes that render the formulation isotonic with the blood of the intended recipient, suspending agents, solubilizers, thickening agents, stabilizers, and/or preservatives.

An effective dose of the composition depends upon many different factors, including means of administration, target site, physiological state of the subject, whether the subject is human or an animal, other medications administered, and the subject requires prophylactic or therapeutic treatment.

Usually, the subject is a human, but the disclosed method also may be performed using nonhuman mammals, including transgenic mammals.

A treatment-effective amount of T cells is typically greater than $10^2$ cells. A treatment-effective amount of T cells is typically less than or equal to $10^{10}$ cells (e.g., less than or equal to $10^9$ cells, less than or equal to $10^8$ cells, less than or equal to $10^7$ cells, or less than or equal to $10^6$ cells), although an amount of more than $10^{10}$ cells also is contemplated. In various aspects, a single dose of T cells will range from about $10^6$ to about $10^9$ cells/kg body weight, including all integer values within those ranges.

The product administered to the subject, in various embodiments, comprises a substantially pure population of the desired cell type (e.g., T cells that target the α-syn mutant). In this regard, the product preferably contains greater than 50%, greater than 60%, or greater than 70% (e.g., greater than 80%, greater than 85%, greater than 90%, or greater than 95%) of the desired cell type(s). For example, the product administered to the subject optionally comprises 70%-95% (or more) T cells activated against the α-syn mutant.

Cells administered to a subject are generally presented in a volume of a liter or less, such as 500 ml or less. In some embodiments, the density of the desired cells is optionally greater than $10^6$ cells/ml, and generally is greater than $10^7$ cells/ml (e.g., generally $10^8$ cells/ml or greater). The cells for administration can be apportioned into multiple administrations (e.g., infusions) that cumulatively provide a single dose.

Administration and Lewy Body Reduction

A composition comprising the T cells specific for an α-syn mutant may be administered orally, topically (e.g., transdermal, etc.), vaginally, rectally, or parenterally (e.g., subcutaneous, intradermal, intrathecal, intramuscular, intrasternal, intracranial, intraperitoneal, or intravenous administration). Preferably, the composition is administered parenterally, e.g., by intravenous or intrathecal administration (injection or infusion). The composition may be administered, prior to, during and/or after another treatment. The disclosure also contemplates a therapeutic regimen wherein multiple doses of T cells are administered to a subject over a period of time, e.g., until a sufficient immune response has been achieved. Typically, the immune response is monitored and repeated dosages are given if the immune response starts to wane. In some methods, reduction in the amount of Lewy Bodies in the central nervous system of the subject or improvement in a clinical symptom of disease is monitored at intervals after administration (e.g., 12 hours, 24 hours, 3 days, 5 days, 7 days, 10 days, 14 days, 21 days, 28 days, 35 days, 42 days, 49 days, 6 months, 7 months, 8 months, 9 months, 10 months, 11 months, one year or longer). Additional doses of composition may be administered to the subject, if needed.

Subjects amenable to treatment include (but are not limited to) individuals exhibiting unwanted Lewy Bodies, at risk a Lewy Body Disorder (LBD) but not showing symptoms (e.g., a subject at genetic risk of developing LBD, having a family history of LBD, and/or displaying biochemical markers of LBD), as well as subjects showing symptoms of an LBD. The Lewy Bodies in the central nervous system may be determined by, e.g., imaging scans, such as single-photon emission computerized tomography (SPECTR), magnetic resonance imaging (MRI),computerized tomography (CT) scan and positron emission tomography (PET)). Individuals suffering from Parkinson's disease can be identified by clinical manifestations including resting tremor, muscular rigidity, bradykinesia and postural instability. Genetic markers of risk toward PD include mutations in the α-synuclein gene, particularly mutations at positions 30 and 53 of the α-synuclein gene.

In some embodiments, the subject is free of clinical symptoms or risk factors any amyloidogenic disease other than one characterized by Lewy bodies. For example, in some aspects, the subject is free of clinical symptoms or risk factors of disease characterized by extracellular amyloid deposits (e.g., Aβ peptide deposits). In this regard, the subject may be free of clinical symptoms and risk factors of Alzheimer's disease, although the disclosure also contemplates administration of the T cells described herein to subjects suffering from Alzheimer's disease. In some methods, the subject has concurrent Alzheimer's and Parkinson's disease.

The administration of a composition described herein results in reduction of Lewy Bodies (i.e., aggregated α-synuclein) in the central nervous system of the subject. In some embodiments, administration of the composition reduces the amount of Lewy Bodies by at least 10% when compared to the amount of Lewy Bodies present in the central nervous system of the subject prior to treatment. In some embodiments, the amount of Lewy Bodies in the central nervous system is reduced by at least 20% (or at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more) when compared to the amount of Lewy Bodies present in the central nervous system pre-treatment. As described elsewhere herein, the amount of Lewy Bodies present in the central nervous system (e.g., spinal cord, brain stem, midbrain, and/or thalamus) can be determined by methods including, but not limited to, DaTs-can (Ioflupane I 123 injection (phenyltropane)), nuclear imaging scans such as single-photon emission computerized tomography (SPECTR), magnetic resonance imaging (MRI),computerized tomography (CT) scan and positron emission tomography (PET). It will be appreciate that by "amount" is meant both the number of individual Lewy Bodies and the size of existing Lewy Bodies. In this regard, shrinkage of existing Lewy Bodies is a positive biological response that confers a therapeutic benefit to subject.

When the subject is susceptible to or otherwise at risk of a LBD, but does not show symptoms, the amount and frequency of administration of the composition is preferably sufficient reduce the risk of Lewy Body formation or delay the onset of disease. When the subject exhibits symptoms or is diagnosed with LBD, the composition is preferably administered in an amount and frequency sufficient to eliminate, at least partially arrest, or improve a clinical symptom of a disease (physiological, biochemical, histologic and/or behavioral symptoms). For example, administration of the composition optionally results in improvement in motor or cognitive function in a subject suffering from Parkinson's disease. The disclosure contemplates an administration regimen which delays or reduces complications and intermediate pathological phenotypes during the development of a LBD.

EXAMPLES

Example 1

Generation of Antigen-Specific T Cells

To determine if the immunogenicity of aberrant α-syn (e.g., A53T mutant) is sufficient to cause potent T cell responses, preliminary experiments were conducted where A53T α-syn-specific T cells were co-cultured overnight with either A53T α-syn expressing target cells (DC2.4 A53T) or GFP expressing target cells (DC2.4 GFP).

Briefly, bone marrow derived dendritic cells (DCs) were electroporated with A53T α-syn RNA (DC2.4A53T), and used to activate and expand A53T α-syn-specific T cells in vitro (T cells+DC2.4A53T). Supernatant was collected and analyzed for cytotoxic cytokines IFNγ and TNFα. IFNγ was significantly increased when A53T α-syn-specific T cells were cultured against A53T α-syn expressing target cells. Upon recognition of cognate antigen, A53T α-syn-specific T cells secrete IFNγ, associated with cytotoxic activity. However, significantly less IFNγ was detected when A53T α-syn-specific T cells were co-cultured against cells that did not express A53T α-syn, (DC2.4 GFP) [p value=0.009]. See FIG. 1.

This data demonstrates feasibility of generating cytotoxic A53T α-syn-specific T cells and that this technology is capable of generating strong immune responses against a single antigen, including the human A53T mutation in α-syn in cell that express the mutation .

Example 2

Delivery of Adoptive T Cells in an Animal Model of α-Synucleinopathy and Survival Effect Following Adoptive T Cell Transfer The M83 transgenic mouse model expresses the human form of the A53T α-syn throughout the neuraxis14. These transgenic mice express the human full-length A53T variant of α-syn and develop severe motor phenotype that typically manifests at about 12-14 months of age (homozygous). Diseased mice exhibit lax grooming, weight loss and subsequently severe movement impairment, limb paralysis, trembling and inability to stand. M83 mice develop widespread α-syn inclusions in the spinal cord, brain stem, midbrain and thalamus, which resemble those observed in human forms of familial PD. The appearance of α-syn aggregates typically coincides with onset of motor impairment.

Figure 2:
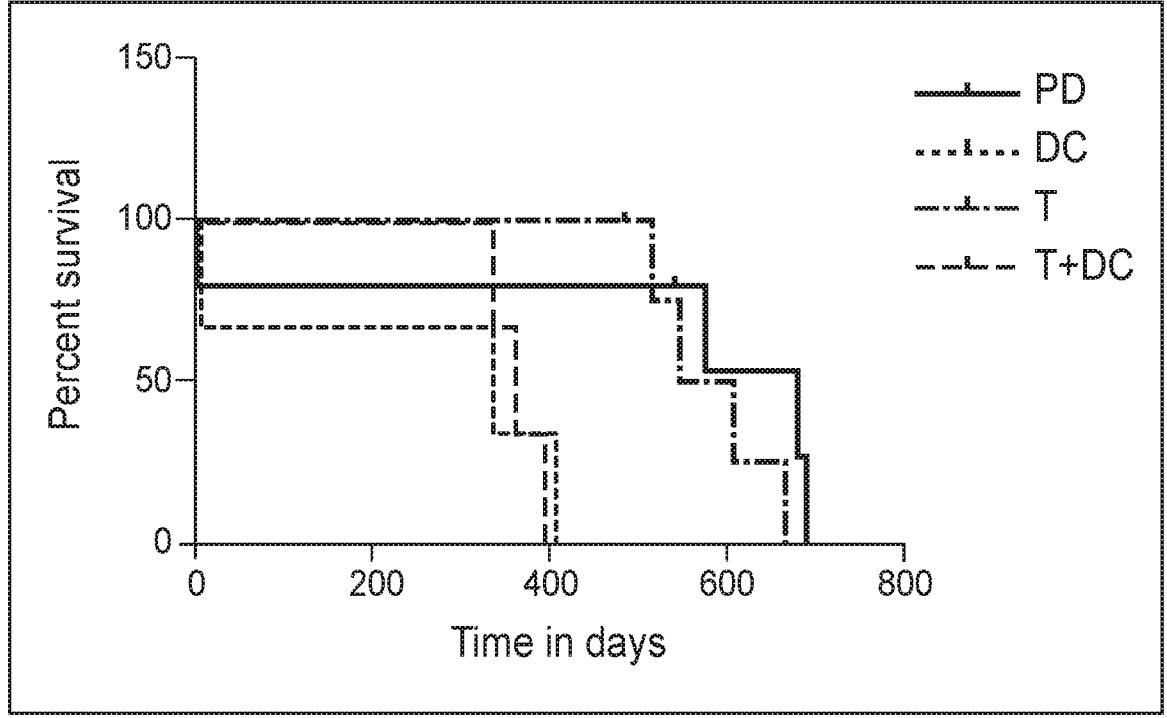
FIG. 2 shows the survival curve of M183 mice treated with A53T α-synuclein specific T cells vs. untreated M83 mice.

M83 mice were divided into 3 groups (n=5 each) and vaccinated with DC vaccine, T cells, or a combination of DC+T cells. After adoptive transfer, mice were observed regularly (health status, weight and time to paralysis) and their survival curve plotted. Mice that were treated adoptively survived significantly longer (19-24 months) than their untreated counterparts. See FIG. 2. Disease control subjects and subjects administered the dendritic cell vaccine survived approximately 400 days; subjects administered T cells survived beyond 600 days, and subjects administered a combination of dendritic cells and T cells survived even longer.

Figure 3:
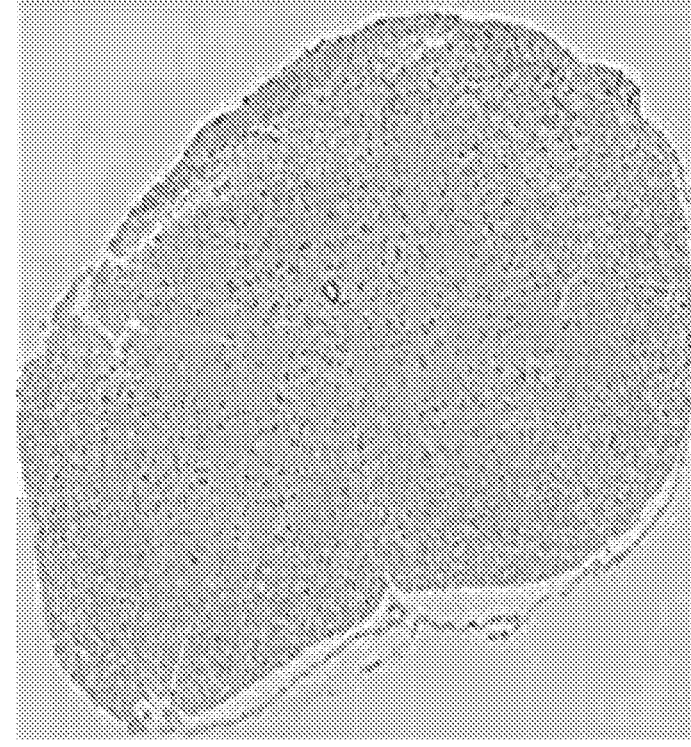
FIG. 3 shows an image of a spinal cord section of a control, untreated mouse (left panel) compared to a mouse treated with A53T α-synuclein specific T cells (right panel).
Figure 3:

M83 mice that were adoptively treated survived past the previously published time point (>12-14 months) and were euthanized after 20 months, before they presented with any motor symptoms. Their brains were excised, and analyzed for α-synuclein expression. Results from immunohistochemical analyses revealed no significant accumulation of α-syn inclusion pathology within neurons of the brain and spinal cord of treated animals (FIG. 3, right panel), when compared with untreated controls (FIG. 3, left panel where darker color=α-syn). This data conclusively demonstrates the feasibility, safety and efficacy of the adoptive T cell therapy described herein in the M83 animal model.

The data provided herein collectively suggests that adoptive transfer of pre-activated T cells is a useful for the treatment of Lewy Body disorders (including, but not limited to Parkinson's Disease) in view of the survival benefit and clearance of α-syn aggregates in the brain and spinal cord of M83 homozygous mice.

Example 3

Efficient Induction of α-Synucleinopathy in the Central Nervous System

Figure 4A:
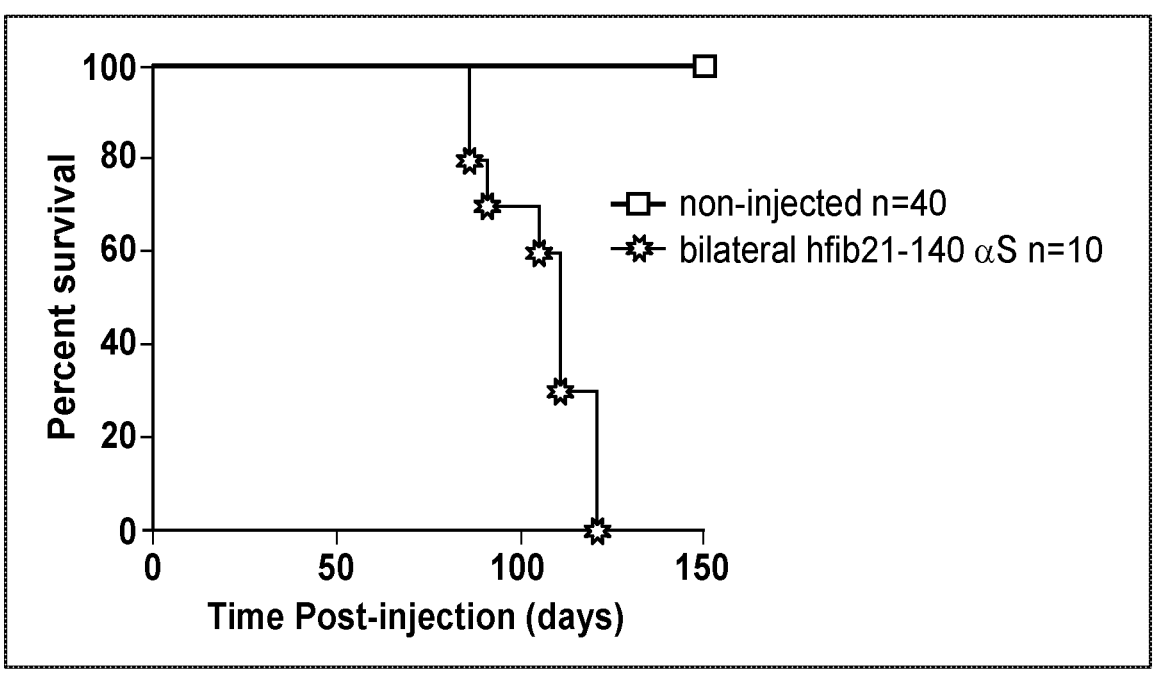
FIG. 4A is a survival plot showing decreased time to terminal state (paralysis) for heterozygous M83 mice bilaterally injected (gastrocnemius muscle) with 10 μg of hfib21-140 α-syn (n=10), compared to non-injected heterozygous M83 mice (n=40). All injected mice reached a terminal state (paralysis) within 121 d postinjection (median 111 d; P<0.0001).

Efficient and rapid induction of α-syn pathology in the CNS can be achieved by peripheral injections of amyloidogenic α-syn intramuscularly (IM) to induce a rapid, lethal motor phenotype (50-120 d incubation time) as described in the literature. Mice injected with fibrillar α-syn in this manner developed α-syn inclusion pathology similar to that seen in aged (>8 mo old), homozygous M83 mice. Heterozygous M83 mice injected bilaterally with α-syn fibrils reach a terminal state (paralysis) within 121 d post-injection (median 111 d) compared with non-injected, heterozygous M83 mice (FIG. 4A).

Example 4

Delivery of Adoptive T Cells in an Animal Model of α-Synucleinopathy and Survival Effect Following Adoptive T Cell Transfer The peripheral injection heterozygous M83 mouse model described in Example 3 was used to test the efficacy of the ACT platform. Twenty M83 heterozygous mice were peripherally injected intramuscularly in the gastrocnemius muscle with α-syn fibrils at 4-6 weeks of age. Out of this, 10 mice received ACT (control, no treatment group), and 10 mice received ACT (ACT, treatment group). One week after IM injection of α-syn fibrils, mice in the treatment group received a booster DC vaccine, 7 days post ACT. Mice were observed regularly after receiving IM injections and subsequent ACT treatment (body condition, weight and time to paralysis), and their survival was plotted. As with the homozygous model, mice that were treated adoptively sur-

Figure 4B:
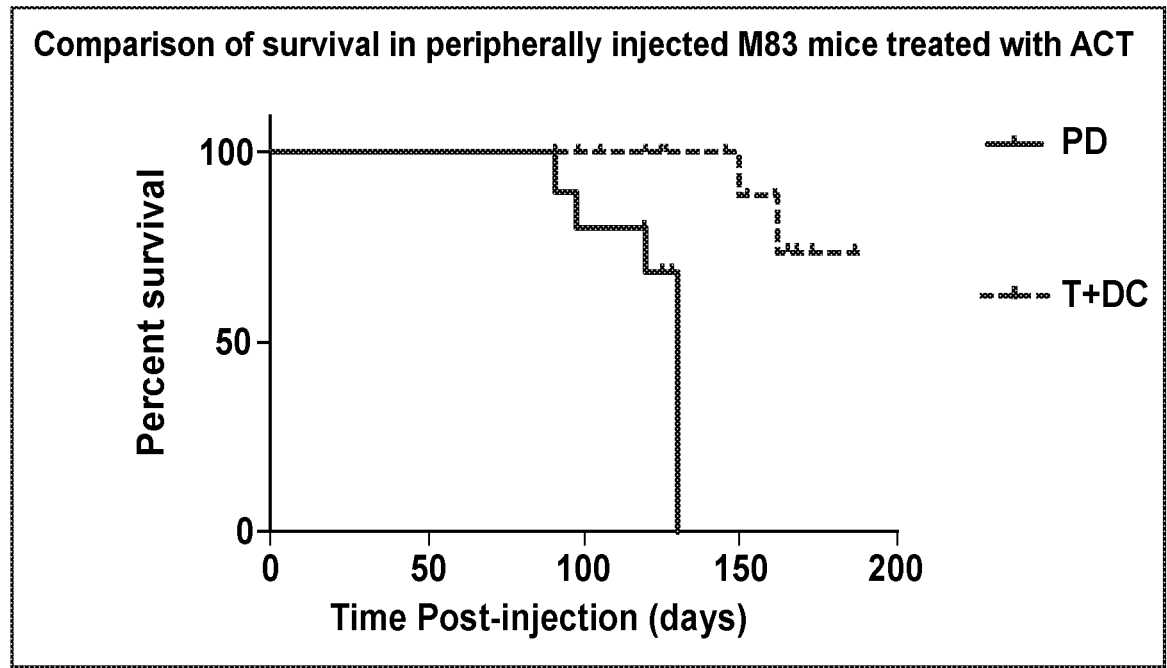
FIG. 4B is a survival plot showing increased time to terminal state (paralysis) for heterozygous, bilaterally injected (gastrocnemius muscle) M83 mice with 10 μg of hfib2l-140 α-syn (n=10) treated with A A53T α-synuclein specific T cells compared to untreated, bilaterally injected (gastrocnemius muscle) heterozygous M83 mice (n=10), (P<0.0001).

12 vived significantly longer (>175 days post injection, P<0.0001) than their untreated counterparts (130 days post injection, FIG. 4B).

Example 5

Delivery of Adoptive T Cells in an Animal Model of α-Synucleinopathy and dMRI Following Adoptive T Cell Transfer Diffusion MRI is a technique for in vivo structural imaging that employs MRI pulse sequences to examine biological tissue wherein the diffusion properties of water in the tissue sample are quantified. Diffusion imaging is sensitive to subtle differences in the mechanical properties of soft tissue and has thus been used widely in neurological studies. Fractional anisotropy (FA) is the primary diffusion metric used and is classically applied to characterize white matter tracts. In white matter, FA quantifies many factors, including axonal density and the degree of myelination.

Figure 5:
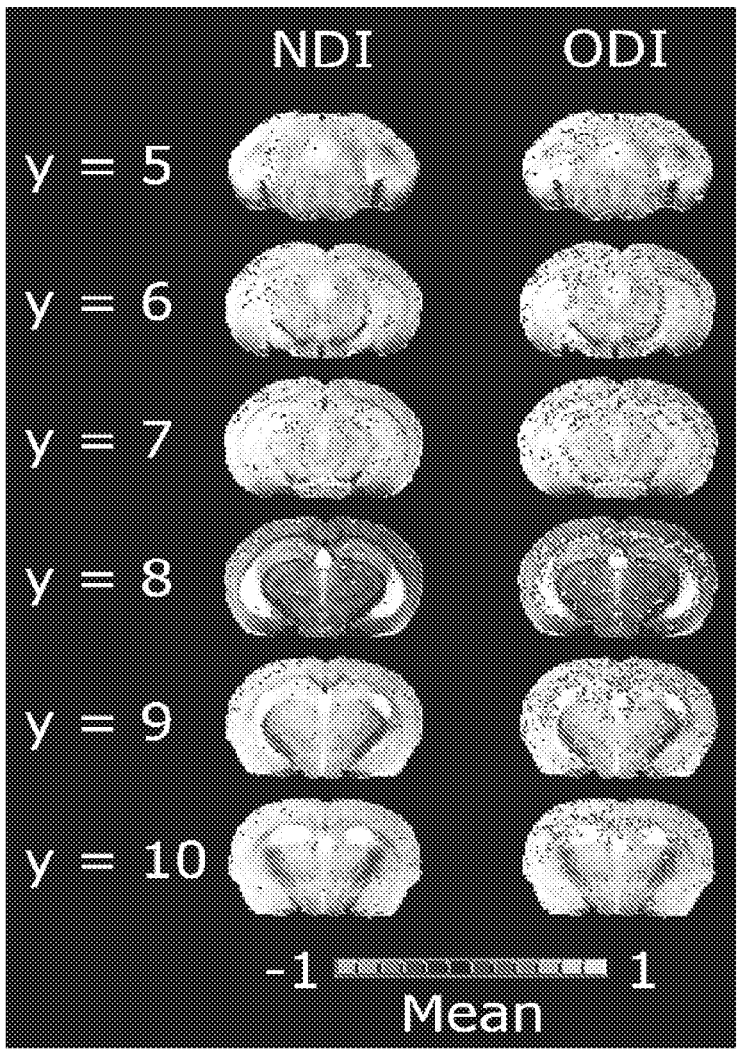
FIG. 5 provides brain scan images showing a significant increase in orientation dispersion index (ODI) or neurite density index (NDI) in αS mice compared to αS mice that received A53T α-synuclein specific T cells.

Peripherally injected α-syn mice and saline injected mice were imaged at baseline and 3 months post-injection. NODDI maps (i.e. orientation dispersion index (ODI) or neurite density index (NDI)) were calculated on diffusion images (FIG. 5). Between-group voxel-wise independent samples t-tests were performed between α-syn-injected and saline-injected groups. Preliminary results indicate that at baseline, few differences exist. At 3-months post-injection, higher neurite density can be seen to have spread in the anterior direction such that they are almost nonexistent in the hindbrain, sparse in the midbrain, and rampant in the cortex. Higher NDI in the α-syn-injected group compared to controls is likely a result of α-syn pathology spreading anteriorly and activating an immune response, leading to neuroinflammation. Similarly, a lowered ODI in the α-syn +ACT treated group compared to the α-syn injected group is suggestive of decreased neurodegeneration, resulting from a lowered burden of α-syn pathology in the cortical regions. This data provides in vivo neuroimaging evidence that PD mice treated with the ACT immunotherapeutic modality likely have less impairment in brain structure.

Each publication, patent application, patent, and other reference cited herein is incorporated by reference in its entirety to the extent that it is not inconsistent with the present disclosure.

What is claimed is:

1. A composition comprising (a) a dendritic cell modified to express, wherein the mutant comprises the amino acid sequence of SEQ ID NO: 1, wherein the alanine at position 53 of SEQ ID NO: 1 is replaced with a threonine, (b) a T cell specific for the α-syn-A53T mutant specifie, and (c) a pharmaceutically acceptable carrier.

2. A method of reducing Lewy Bodies in the central nervous system of a subject, the method comprising administering to a subject in need thereof the composition of claim 1 in an amount effective to reduce Lewy Bodies in the subject.

3. The method of claim 2, wherein the T cell is derived from the subject.

4. The method of claim 2, wherein the subject has a disorder selected from the group consisting of Parkinson's Disease, multiple system atrophy, Lewy Body dementia and Alzheimer's Disease.

5. The method of claim 2, wherein Lewy Bodies are reduced in the brain of the subject following administration.

6. The method of claim 2, wherein Lewy Bodies are reduced in the spinal cord of the subject following administration.

7. The method of claim 2, wherein Lewy Bodies are reduced by at least 20%.

* * * * *

SEQUENCE LISTING

```
<160> NUMBER OF SEQ ID NOS: 1

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
```

-continued

```
65                    70                    75                    80

Thr Val Glu Gly Ala Gly Ser Ile Ala Ala Ala Thr Gly Phe Val Lys
                85                    90                    95

Lys Asp Gln Leu Gly Lys Asn Glu Glu Gly Ala Pro Gln Glu Gly Ile
            100                   105                   110

Leu Glu Asp Met Pro Val Asp Pro Asp Asn Glu Ala Tyr Glu Met Pro
            115                   120                   125

Ser Glu Glu Gly Tyr Gln Asp Tyr Glu Pro Glu Ala
    130                   135                   140
```